United States Patent [19]

Fedeli et al.

[11] Patent Number: 4,985,552

[45] Date of Patent: Jan. 15, 1991

[54] PROCESS FOR OBTAINING CHEMICALLY DEFINED AND REPRODUCIBLE POLYDEOXYRIBONUCLEOTIDES

[75] Inventors: Gianfranco Fedeli, Milan; Giuseppe Diamantini, Ap iano; Gentile; Marisa Maontovani, Villas Guardia; Giuseppe Prino, Milan, all of Italy

[73] Assignee: Crinos Industria Farmacobiologica S.p.A., Villa Guardia, Italy

[21] Appl. No.: 374,561

[22] Filed: Jul. 5, 1989

Related U.S. Application Data

[63] Continuation of Ser. No. 36,996, Apr. 10, 1987, abandoned.

[30] Foreign Application Priority Data

Apr. 17, 1986 [IT] Italy ............................... 20117 A/86

[51] Int. Cl.$^5$ ............................................... C07N 1/00
[52] U.S. Cl. ........................................ 536/27; 536/28; 536/29
[58] Field of Search .................. 536/27, 28, 29; 514/44

[56] References Cited

U.S. PATENT DOCUMENTS

| | | | |
|---|---|---|---|
| 3,314,937 | 4/1967 | Vendrely et al. | 536/27 |
| 3,829,567 | 8/1974 | Butti et al. | 536/24 |
| 3,899,481 | 8/1975 | Butti et al. | 536/28 |
| 4,216,293 | 8/1980 | Fedeli et al. | 435/268 |
| 4,649,134 | 3/1987 | Bonomini | 514/44 |
| 4,693,995 | 9/1987 | Prino et al. | 514/44 |

FOREIGN PATENT DOCUMENTS

| | | |
|---|---|---|
| 2131249 | 11/1972 | France . |
| 2131248 | 11/1982 | France . |
| 0004308 | 1/1980 | Japan ..................... 514/44 |
| 0652187 | 3/1979 | U.S.S.R. ................. 514/44 |

OTHER PUBLICATIONS

Cizmeci et al., The Chemical Abstracts, 107:147033z (1987).

*Primary Examiner*—John W. Rollins
*Assistant Examiner*—James O. Wilson
*Attorney, Agent, or Firm*—Armstrong, Nikaido, Marmelstein Kubovcik & Murray

[57] ABSTRACT

By carrying out the depolymerization of stabilized solutions of highly polymerized and nicked polydeoxyribonucleotides, as obtained through stabilizing aggregation of raw nucleic acids, the depolymerization being carried out by heating at controlled temperature and being controlled as a function of the variation of the reversible hyperchromicity, followed by the removal of the hydrogen bonds in the double stranded filaments and by thermal stabilization of the single stranded filaments, the polydeoxyribonucleotide, known as Defibrotide is obtained. Defibrotide has the following formula of random sequence:

$$P_{1-5},(dAp)_{12-24},(dGp)_{10-20},(dTp)_{13-26},(dCP)_{10-20},$$

wherein
P = phosphoric radical
dAp = deoxyadenylic monomer
dGp = deoxyguanylic monomer
dTp = deoxythymidylic monomer
dCp = deoxycytidylic monomer and has well defined chemico-physical properties, reproducible in the industrial production.

37 Claims, 1 Drawing Sheet

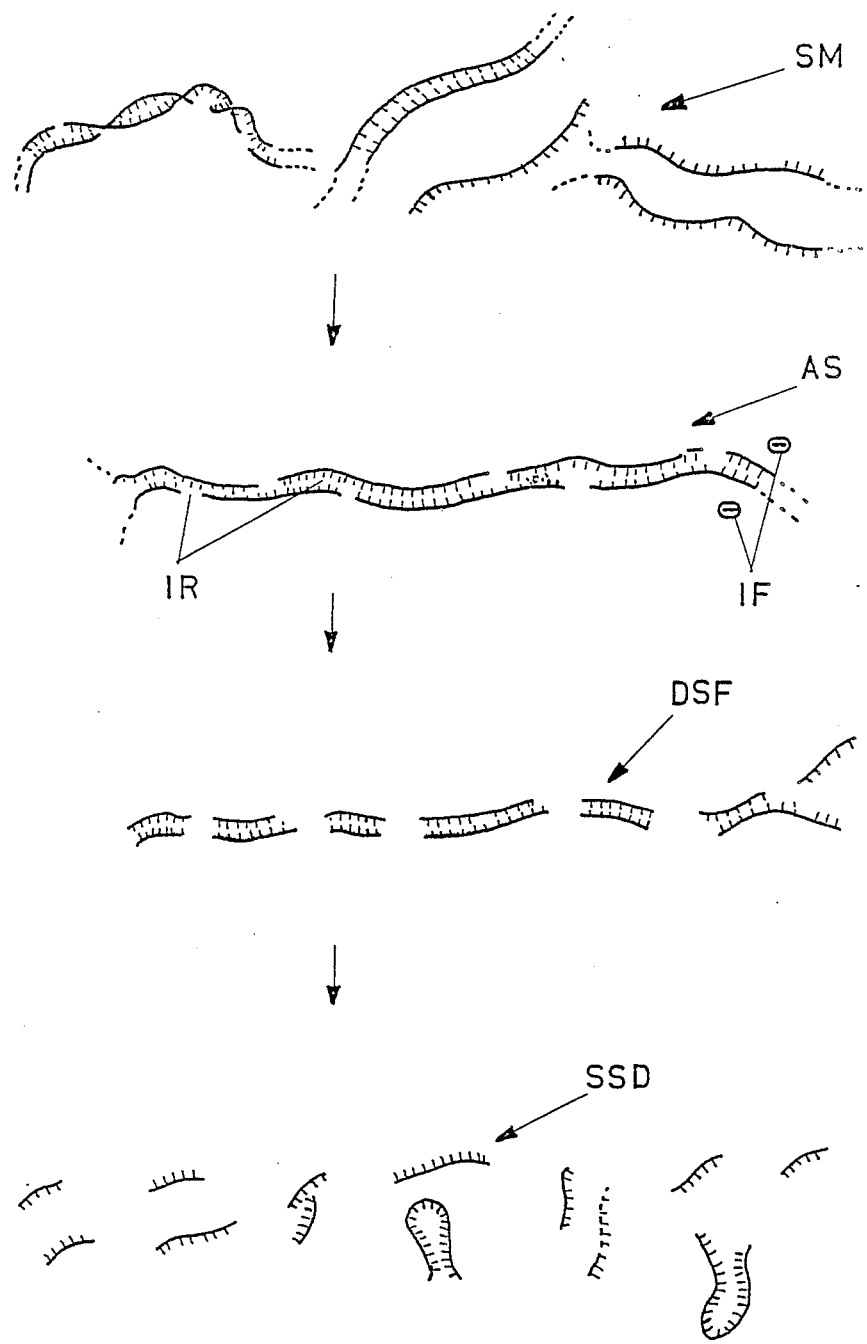

PROCESS FOR OBTAINING CHEMICALLY DEFINED AND REPRODUCIBLE POLYDEOXYRIBONUCLEOTIDES

This application is a continuation of application Ser. No. 036,996 filed Apr. 10, 1987, now abandoned.

DESCRIPTION

The present invention relates to the preparation of polydeoxyribonucleotides in a chemically defined and reproducible form.

More specifically the present invention relates to the preparation of the substance known under the name of Defibrotide (DCI, liste 21, Chronique OMS 35, 5 suppl. 4, 1981).

The substance named Defibrotide is defined as a sodium salt of low molecular weight nucleotidic fractions obtained by extraction from animal organs as disclosed in U.S. Pat. Nos. 3,770,720 and 3,899,481, the disclosures of which are hereby incorporated by reference.

Defibrotide has been the subject of a number of pharmacological and clinical studies which on one side permitted its very low toxicity (both acute and subacute as well as chronical) to be assessed, with the self-evident advantages from the point of view of the possible therapeutical uses, whereas on the other side Defibrotide disclosed remarkable and fully unforeseeable therapeutical properties. As a matter of fact, as described in U.S. Pat. No. 3,892,567, the disclosure of which is hereby incorporated by reference, Defibrotide is endowed with a fibrinolytic activity making it useful as an antithrombotic drug. Moreover the pharmacological and clinical experimental work (as carried out on volunteers) showed the following activities:

(a) therapy of the peripheral arteriopathies (inventor: O. N. Ulutin; U.S. patent application Ser. No. 649,055 filed on Sept. 10, 1984), now abandoned;

(b) treatment of acute renal insufficiency (inventor: V. Bonomini; U.S. Pat. No. 4,649,134, granted on Mar. 10, 1987);

(c) treatment of miocardial acute ischemia (inventors: G. Prino, M. Mantovani, R. Niada; U.S. Pat. No. 4,693,995 filed on Feb. 14, 1985).

The disclosures of the above patent and patent applications are hereby incorporated by reference for the teaching of pharmaceutical compositions and uses disclosed therein.

The variety and importance of the above mentioned therapeutical uses obviously caused the attention to be concentrated on Defibrotide and on the industrial production thereof. This research work was particularly directed on one side to production taking place on an industrial scale economically advantageous and technically reasonable, and on the other side to the standardization and the control of the resulting industrial product Defibrotide.

Otherwise stated the processes forming the subject of the above mentioned U.S. Patents are those which were initially developed, leading to the obtention of the nucleotidic structure to which the name Defibrotide was given.

When the results of the pharmacological and clinical studies revealed the extremely interesting and multiform properties of the initially isolated substance, as it is natural and evident, on one side the problem of the production on industrial scale was faced, and on the other side the studies of the chemical and physical properties of the substance Defibrotide were closely considered since they are strictly connected to the production and to the requirements thereof.

It has been thus found and is a first feature of the present invention that Defibrotide does fully fulfill the above indicated pharmacological and therapeutical properties and is therefore particularly suitable for the above cited therapeutical uses, if the nucleotidic fractions forming it are in stoichiometrical agreement with the following polydeoxyribonucleotidic formula of random sequence:

$$P_{1-5}, (dAP)_{12-24}, (dGp)_{10-20}, (dTp)_{13-26}, (dCp)_{10-20}$$

wherein
P = phosphoric radical
dAp = deoxyadenylic monomer
dGp = deoxyguanylic monomer
dTp = deoxythymidylic monomer
dCp = deoxycytidylic monomer The Defibrotide corresponding to this formula moreover shows the following chemico-physical properties:

electrophoresis = homogeneous anodic mobility;

extinction coefficient, 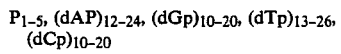 at $260 \pm 1$ nm = $220 \pm 10$;

extinction ratio, $E_{230}/E_{260} = 0.45 \pm 0.04$;

coefficient of molar extinction (referred to phosphorous), $\epsilon(P) = 7.750 \pm 500$;

rotatory power $[\alpha]_D^{20°} = 53° \pm 6$;

reversible hyperchromicity, indicated as % in native DNA, $h = 15 \pm 5$.

The reversible hyperchromicity is a peculiar optical property of the polydeoxyribonucleotides and is a measure of the capacity of these biopolymers of molecule rearrangement in solution.

As a function of thermodynamic status, the molecules of a substance tend to have a disorderly and free motion and the higher the temperature of the solution of the substance the higher the speed of the motion. In most of the simple, soluble substances (salts, sugars, peptides), as the temperature decreases, even if the motion speed diminishes, a rearrangement of the molecules compared to the initial conditions does not take place. In the case of the biopolymers, like the polydeoxyribonucleotides, the molecules tend to a mutual rearrangement. This property is very evident in the double helix DNA, wherein the capability of rearrangement compared to the initial condition can be of the order of 100%. The measurement of this capacity can be carried out in a specific way for the polydeoxyribonucleotides by means of measurements of the variations of optical density (O.D.) at 260 nm of solutions which are heated and cooled or made alkaline and neutralized at pH 5.

The measurement of the hyperchromicity is given by the following formula:

$$h = \frac{O.D. \text{ (hot or at alkaline pH)}}{O.D. \text{ (at room temperature or neutral pH)}} - 1$$

which in view of the above statement, can be also defined as:

$$h = \frac{O.D. \text{ (in disorderly phase)}}{O.D. \text{ (in orderly phase)}} - 1$$

In this manner the hyperchromicity h indicates the fraction of the molecules of the polynucleotide capable of rearrangement.

As already mentioned in the case of double helix DNA this value, indicated as a percentage, can be of the order of 100%, whereas in the case of oligodeoxyribonucleotides (molecular weight lower than 8,000 dalton) this value is almost zero.

It has been now found that the optimum value of h, in order that the polydeoxyribonucleotide Defibrotide is pharmacologically active and suitable for the above therapeutical uses, must correspond to a percentage of about 15% and that values of h less than 10% involve a dramatic reduction of the pharmacological activity, whereas values of h higher than 20% involve risks of undesirable side effects.

These characteristic limits of hyperchromicity indicate that the polydeoxyribonucleotide Defibrotide is a single-strand filament and this is confirmed also by the measurements of molecular weight as carried out under diffused light, in which no significant differences of the molecular mass are revealed, operating both under normal conditions and under denaturating conditions.

Consequently the polydeoxyribonucleotide Defibrotide has the structure of a single filament biopolymer with a capacity of intramolecular rearrangement (pairing of nucleic bases within the same molecule) of about 15% indicated in native DNA.

As previously mentioned one of the man features of the present invention resides in the process for the preparation of Defibrotide having the above indicated properties wherein at the same time there are provided substantially perfect uniformity of the product characteristics from one production batch to another, the complete usefulness and reliability of the obtained product for therapy in human beings and, obviously, feasibility and convenience from the viewpoint of industrial production. As already indicated, the process disclosed in U.S. Pat. Nos. 3,770,720 and 3,899,481 comprises the extraction and the partial degradation of the deoxyribonucleic acids by means of protonic degradation of the nucleic acids. In such a process the yields of Defibrotide are relatively low and the product is often accompanied by degradation products. As a matter of fact it is known that the protonic degradation of polydeoxyribonucleotides may induce in a more or less remarkable manner the depurinization, with the risk of having even modest amounts of apurinic acids, which may be toxic, to be formed.

The main purpose of the present invention is thus the essential solution of these problems and drawbacks of previous processes.

A more specific purpose of the present invention is that of providing a process for obtaining Defibrotide having the above indicated chemical and chemico-physical properties.

A further purpose of the present invention is moreover that of providing a process for the production of Defibrotide permitting the use of a number of starting natural materials, in addition to the bovine lung as contemplated in the above indicated patents.

It has been now suprisingly found that by operating under more controlled conditions of aggregation, raw nucleic acids can be depolymerized in advantageous manner, thereby reducing to a minimum the formation of degradation products.

The process according to the present invention is characterized by the following steps:

(a) grinding and hot proteolysis of the starting animal organ;
(b) filtration and concentration of the lysate;
(c) addition to the concentrate of the salt of a cation capable of precipitating phosphates, and adjusting the pH to acidic values not higher than pH 4.5;
(d) filtration under constant volume of the precipitate suspension, in order to separate the polysaccharidic fraction present in solution;
(e) addition to the resulting suspension of insoluble salts of nucleic acids of a hydrosoluble salt of an alkali metal in order to solubilize the nucleic acids, and elimination from the solution of displaced insolubilizing cations;
(f) adjustment of the ionic force of the solution of nucleic acids to a predetermined value at least 1 molar in order to start their stabilizing aggregation in the form of highly polymerized nicked polydeoxyribonucleotides and adjustment of the pH of the same solution until the spectrophotometric analysis of the reaction mixture indicates the maximum reversible hyperchromicity, namely the maximum possible aggregation, has been achieved;
(g) heating of this solution up to the depolymerization temperature of the aggregated polydeoxyribonucleotide, and controlling the depolymerization through the measurement of the variation of the reversible hyperchromicity until it achieves the value, indicated in percent native DNA, of $15 \pm 5$;
(h) stopping by cooling the depolymerization process and removal of the hydrogen bonds in the double filament fragments;
(i) stabilizing the resulting single filament fragments in such condition by heating the resulting solution of the previous step at a temperature and pH higher than those of the depolymerization step thereby preventing the hydrogen bonds from reforming;
(j) hot filtration and removal, still under hot conditions, of the salts present in solution, with possible concentration.

Taking now into consideration the single steps of the above defined process, the animal organs used comprise organs, tissues and cells of mammals, particularly lung, intestin, liver and mucosae of cattle, sheep, swine and horses.

Likewise useful are the residual mother liquors obtained in the production of heparins, proteic lysates and organ extracts. A further starting material comprises cells, such as for example white corpuscles or residues of their culture, spermatozoa, spermatocytes and germinal cells of mammals.

The proteolysis is carried out in a per se known manner with a proteolytic enzyme, such as for example papain, tripsin, etc.

The condition and the duration of the proteolysis obviously depend on the type of proteolytic enzyme and are well known and well generally be within the range of 10°-90° C. for 0.5-10 hours.

For example with papain the proteolysis is generally carried out for 4 hours at 65° C.

Considering now the step b of filtration and that of concentration, the latter is preferably carried out on a membrane with tangential flow. In this manner as a matter of fact it is possible to select a range of desired molecular weights to be obtained. The membrane is thus selected with a well determined cut-off (generally 50,000–100,000).

The resulting concentrate is mixed (step c) with a cation capable of precipitating phosphates in the concentrate. A salt of the cation such as, for instance, halides, sulphates, bicarbonates, acetates of Ca, Zn, or the like, may be added to the concentrate, the pH being adjusted to acidic values.

The precipitate suspension is filtered by diafiltration at constant volume (step d) through a membrane having a pore size of 0.45 µm or less with tangential flow, and with continuous make up of water to keep the volume constant until the polysaccharidic substances disappear from the filtrate.

The hydrosoluble salt, added (in the step e) to the suspension of insoluble salts of nucleic acids, is a salt such as a halide or acetate of an alkali metal, such as sodium or potassium.

In the resulting suspension the insolubilizing cation (such as Ca, Zn, etc.) remains which is removed preferably by diafiltration at constant volume through a membrane having cut-off less than 10,000, with tangential flow and continuous make up of the salt solution to keep the volume constant.

This treatment is continued until in the permeate the insolubilizing cation is no longer present. Alternatively the insolubilizing cation is removed by ion exchange carried out on the suspension resulting from step d.

The solution of raw nucleic acid is adjusted if necessary to an ionic strength at least 1 molar and preferably 3 molar, preferably by the addition of a hydrosoluble salt of an alkali metal, and the pH of the solution is adjusted until the pH value is achieved which according to the experimental measurements corresponds to the maximum reversible hyperchromicity of the system. Such a pH is normally between 4 and 5.

In this step the raw nucleic acids have undergone stabilizing aggregation to form highly polymerized nicked polydoexyribonucleotides.

Step a–c can conveniently be conducted at room temperature, although the temperature can range from 10° to 90° C.

After the step of stabilizing aggregation (step f), the depolymerization of the highly polymerized nicked polydeoxyribonucleotides takes place by heating to a temperature which is preferably about 70°–75° C., although the depolymerization temperature can range from 60° to 90° C., with the depolymerization being monitored by means of measurements of variation of reversible hyperchromicity.

The removal of the remaining hydrogen bonds in the resulting double filament fragments, once the depolymerization is stopped by cooling to a lower temperature, preferably from 15° to 30° C., is carried out by alkalinization of the reaction mass to a pH higher than 7, preferably to a pH of 8 or more.

Lastly the stabilization of the single filament fragments is obtained by heating the solution obtained in step h to a temperature of at least 5° C. higher than that of the depolymerization temperature, and generally to a temperature of 65° to 100° C.

The drawing illustrates, schematically and with the conventional representation, the modifications in various steps of the raw nucleic acids as extracted from organs and subjected to proteolytic digestion.

As it can be clearly observed, when the starting material, which can be imagined as a polynucleotidic assembly which is more or less unpaired, despiralized and partially degraded with formation of short depurinated lengths, indicated by the abbreviation SM, is dissolved in saline solution having high ionic force and being sufficiently protonated, preferably 3 molar, of a hydrosoluble salt of an alkali metal, the molecules forming the starting material tend to aggregate as it is known according to the Chargaff rule of the base pairing, due to the hydrogen bonds available from the solvent medium. Since the polynucleotide chains are partially incomplete, a casual pairing takes place, leading to the formation of highly polymerized double filament polynucleotides, which filaments are casually interrupted by discontinuities in the sequences ("nicks") provided along the hydrophylic borders of the structure represented by the abbreviation AS (aggregated system) in the drawing. In the drawing the hydrorepelling areas (IR) and the hydrophylic areas (IF) having negative charges are illustrated.

At that point the supplying of suitably adjusted thermal energy causes a fracture, prevailingly at the level of the discontinuities only of the double filaments, to occur, whereby double filament fragments having a certain regularity (indicated as DSF in the figure) are produced.

The fragmenting degree is monitored through the control of several chemico-physical parameters, the main one being the index of reversible hyperchromicity of the system (as already defined).

The removal of the hydrogen ions, carried out at the time at which the reversible hyperchromicity has achieved the value characterizing Defibrotide, (15±5) causes the hydrogen bonds, by which the nucleic bases are paired, to be removed, thus resulting in polydeoxyribonucleotidic mono-filaments with the desired characteristic structure.

It has been also found that the condition of freedom of the single filaments is stabilized in the structure, with the single filaments having about 15% of reversible hyperchromicity which characterize Defibrotide, when the solution is further heated at pH 8±0.2 at a temperature level higher than the temperature used in the depolymerization under aggregating conditions which previously took place.

The kinetic energy induced in the system prevents the reaggregations, which might occur in the subsequent phases of the process involving isolating the polydeoxyribonucleotidic fractions of interest, from taking place.

Only the polydeoxyribonucleotidic filaments thus stabilized (indicated by SSD in the figure) maintain all the chemical properties which characterize the desired Defibrotide structure.

By operating in this manner the degree of depurination is reduced to a minimum and the ratio between purinic bases and pyrimidinic bases rarely is less than 0.95%.

It is lastly to be pointed out that with the process according with the present invention it is possible to obtain standardized polydeoxyribonucleotides exhibiting the chemical and pharmacological properties of Defibrotide. In the course of this research work it has been found as already mentioned that it was possible to obtain polydeoxyribonucleotides having the desired properties also from other sources in addition to bovine lung. It has been now surprisingly found that, by operating according to the above indicated criteria, it is possible to obtain polydeoxyribonucleotides having the characteristics of Defibrotide, also from other sources such as swine lung and intestine, liver and thymus, both of cattle or swine. This possibility is very important since in view of anticipated therapeutical consumption of the product Defibrotide, it seems necessary to broaden the starting sources. It is particularly advantageous to be able to use the mother liquors of heparine production, extracts and proteic hydrolysates as starting materials, as those material are very abundant and to date scarcely used, their disposal being also a serious cause of pollution.

Another advantage of the present invention is not only by the possibility of broadening the Defibrotide extraction sources, but also by the possibility of recovering Defibrotide from by products, other processes being thus rendered more economical, such as processes for producing heparin and proteic lysates and moreover reducing the causes of pollution such as that resulting from phosphate rich residues of these other processes, which residues, in fact, are of nucleic origin.

The following examples illustrate in a non limiting manner how the claimed process can be carried out.

EXAMPLE 1

100 kg of frozen bovine lung were ground and dispersed in 50 liters of potable water containing 200 g of raw papaine, activated with sulphites. The pH of the dispersion was adjusted to 5.8 with diluted hydrochloric acid, the mass being then heated to 65° C. to carry out the proteolysis. After 4 hours the proteolysis was stopped by heating the mass to boiling for 15 minutes. After filtration through a filter press, in which the solids in the dispersion were removed, the filtered solution of proteolysate was concentrated to a volume of 25 liters by filtrating with tangential flow on a tubular membrane Romicon with a cut-off of 50,000. The permeate, having a heparinic activity of about 8 UI/ml, could be used in the recovery of heparine and aminoacids.

The concentrate was treated with 150 g of anhydrous calcium chloride, and the solution was adjusted to pH 3 to cause the nucleic portion to be precipitated, whereas the remaining polysaccharidic portion remains in the solution.

The suspension was diafiltered by tangential flow through a tubular membrane Romicon of 0.45 micron porosity, keeping constant the volume of the concentrate by additions of a solution of 0.01 calcium chloride. The diafiltration was continued until the concentrate no longer produced a reaction of the polysaccharides with cetylpyridinium chloride.

The diafiltration permeate was used for the recovery of polysaccharides, producing about 50 gr of a mixture consisting of condroitin sulphates and heparin.

The suspension of diafiltration concentrate, containing the insoluble calcium salts of nucleic acids, was mixed with 25 liters of 3M sodium chloride. The mixture was diafiltered with tangential flow through a membrane Romicon with cut-off of 10,000, the volume of concentrate being maintained constant by additions of 3 molar solution of sodium chloride until the permeate liquid no longer produced the reaction of the calcium with ammonium oxalate; in this way the exchange between calcium and sodium ions occurred to convert all the nucleic acids into the sodium form.

The concentrate was then further concentrated by filtration with tangential flow on the same membrane until a volume of 7.5 liters was obtained. This concentrate contained about 3% (spectrophotometric evaluation) of sodium salts of the raw nucleic acids, corresponding to 0.22% of the starting organ weight, in a 3 molar saline solution.

This solution was adjusted to the point of maximum hypochromicity by adding portions of 3M hydrochloric acid until the spectrophotometric measurements of hyperchromicity through realkalinization of the samples of solution did not show a maximum delta of absorption; the latter was found equal to 38% of native DNA when the pH reached 4.25, thus corresponding to the point of maximum hypochromicity of the system and consequently to the maximum state of aggregation and pairing of the bases of the polydeoxyribonucleotidic acids in solution.

When such a condition was established, the solution was heated up to 75° C. to start the depolymerization.

At 15 minutes intervals, measurements of hyperchromicity on samples of the solution were carried out to monitor the progress of the depolymerization. After six measurements, the data reported on the ordinates of a Cartesian system permitted the extrapolation on the abscisse of a time of 4 hours to obtain polydeoxyribonucleotides having a hyperchromicity of 19% in native DNA.

Consequently after 4 hours the depolymerization under aggregating conditions was stopped, by cooling the depolymerized mass to a temperature of 30° C. and making it alkaline (pH 8) with 3 molar sodium hydroxide.

The temperature was raised up to 85° C. for 30 minutes in order to stabilize the structure of the polynucleotides, and thereafter the solution was hot filtered and subjected to dialysis and concentration with tangential flow as above to a volume of 6500 ml.

The resulting product was precipitated with alcohol from the concentrated solution.

After dehydration with alcohol and drying under vacuum at 60° C., there was obtained 126 g of product having the following analytical properties:

| P = 8.40% | G = 8.60% |
|---|---|
| d = 34.10 | C = 6.15% |
| A = 8.90% | T = 9.20% |

P/(A+G+C+T) mol=1.07
Purines/pirymidines mol=0.96
molar estinction referred to P $\epsilon(P)=7.800$
extinction coefficient $E_1\%_{cm}=230$
rotatory power $[\alpha]_D^{20°}=+57°$
hyperchromicity (in native DNA) h=18%

The above reported data stoichiometrically lead to the following nucleotidic formula:

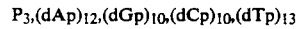

$P_{35}(dAp)_{12}(dGp)_{10}(dCp)_{10}(dTp)_{13}$

EXAMPLE 2

1000 kg of swine lung were processed as described in the example 1, to produce 700 g of Defibrotide with the following properties:

| P = 8.50% | G = 8.90% |
|---|---|
| d = 36.20% | C = 6.80% |
| A = 9.30% | T = 10.20% |

P/(A+G+C+T) mol=1.02
purines/pyrimidines mol.=0.90

| | | |
|---|---|---|
| $[\alpha]_D^{20°} = +53°$ | $h = 16\%$ | $\epsilon(P) = 7.750$ |

The above reported data stoichiometrically lead to the following nucleotidic formula:

P,(dAp)$_{12}$,(dGp)$_{10}$,(dCp)$_{10}$,(dTp)$_{14}$

EXAMPLE 3

1000 liters of mother liquors coming from the production of heparin from bovine intestinal mucosa were concentrated by tangential flow membrane to 55 liters.

The nucleic acids were precipitated with zinc chloride as described in U.S. Pat. No. 3,770,720. After decantation and washing to separate the polysaccharides, the precipitate was suspended in water and converted into the sodium salt by treatment with ion exchange resin IR 120 in Na+ form.

The sodium salts of the nucleic acids contained in the eluate were aggregated by adding an equal volume of a 5M solution of acetate buffer (pH 3.9) thus obtaining a final mixture, having a pH 4.1, which was used for the measurement of the maximum reversible hyperchromicity of the system.

The mixture was heated to 70° C., and maintained at that temperatures with the index of reversible hyperchromicity being monitored every 15 minutes. After 4 hours the index achieved a value h=18%. The solution was cooled to 25° C. and then adjusted to pH 7.8 with 5N sodium hydroxide and then heated to 85° C. for 30 minutes. After filtration 1.0 volume of the product was precipitated by adding 1.5 volumes of ethanol. The precipitate was subsequently washed and dehydrated with ethanol, and thereafter dried under vacuum at 60° C.

630 g of product were obtained with the following chemical properties:

| | |
|---|---|
| P = 8.73% | G = 8.5% |
| d = 36.40% | C = 6.9% |
| A = 9.60% | T = 9.7% |

P/(A+G+C+T+) mol.=0.4
purines/pyrimidines mol=0.92

| | | |
|---|---|---|
| $\epsilon(P) = 7.580$ | $[\alpha]_D^{20°} = 51°$ | $h = 15\%$ | to which the following nucleotidic formula corresponds:

P$_2$(dAp)$_{13}$,(dGp)$_{10}$,(dTp)$_{14}$,(dCp)$_{11}$

EXAMPLE 4

30 kg of sodium salts of nucleic acids obtained from bovine lung according to the disclosure of U.S. Pat. No. 3,770,720, were dissolved in 500 liters of 3M acetate buffer at pH 4.5 to form a solution having the maximum reversible hyperchromicity of the system.

The thus obtained solution was filtered and then heated to 75° C. At 15 minutes intervals samples are taken for the determination of the index of reversible hyperchromicity, and the hyperchromicity data was recorded on the ordinates of a Cartesian system wherein on the abscisse the times at which the samples were taken were reported.

On the basis of the data found for 3 or 4 measurements, the time necessary for the hyperchromicity h of the system to achieve a value of 15%, indicated in native DNA, was extrapolated, and the heating was continued for that time.

The resulting mass was adjusted to pH 8 with 5N sodium hydroxide and heated to 80° C. for 60 minutes to stabilize the polydeoxyribonucleotidic structure, which is characteristic of Defibrotide.

Finally the solution was filtered and dried as disclosed in example 3. About 15 kg of product was obtained. The properties of the product prepared as described in this example were the following:

| | |
|---|---|
| P = 8.83% | G = 8.40% |
| d = 37.80% | C = 7.00% |
| A = 9.90% | T = 9.85% |

P/(A+G+C+T) mol=1.06
purines/pyrimidines mol=0.95

| | | |
|---|---|---|
| $\epsilon(P) = 7.750$ | $[\alpha]_D^{20°} = +54°$ | $h = 17\%$ |

The resulting nucleotidic formula was:

P,(dAp)$_{13}$,(dGp)$_{11}$,(dTp)$_{14}$,(dCp)$_{12}$

EXAMPLE 5

A modification of example 4 involved removing, during the depolymerization step, from the system of the depolymerized product, by means of permeation on a tangential flow membrane with a molecular cut-off of 100,000; This removal was made in order to avoid further degradation for polydeoxyribonucleotidic structures which might already have the structure of Defibrotide, thus improving the yields.

In fact by operating under the same conditions as in example 4, but with this modification from 30 kg of sodium salts of nucleic acids there were obtained 16.5 kg of product with properties corresponding to those of example 4.

We claim:

1. A process for producing the polydeoxyribonucleotide Defibrotide from a solution of raw nucleic acids obtained from mammalian cells, said solution being substantially free of polysaccharides and proteins, said process comprising the steps of:
   (1) forming highly polymerized nicked polydeoxyribonucleotides by stabilizing an aggregation of the raw nucleic acids by adjusting the ionic strength and the pH of the solution until the maximum reversible hyperchromicity has been reached;
   (2) depolymerizing the polydeoxyribonucleotides until the reversible hyperchromicity of the solution is at a value of h=15±5, measured as a percent in native DNA, by heating the resulting solution to a depolymerizing temperature for the said polydeoxyribonucleotide, and maintaining the solution at a depolymerizing temperature until said specified reversible hyperchromicity value has been achieved;
   (3) terminating the depolymerization reaction by cooling, and removing the hydrogen bonds in any double filament fragment in the depolymerized solution by making the medium alkaline, thereby forming single filament polydeoxyribonucleotide fragments; and (4) stabilizing the resulting single filament fragments of polydeoxyribonucleotides by heating the resulting solution at a temperature and pH higher than those of the depolymerization reaction to prevent hydrogen bond reformation.

2. A process according to claim 1, wherein step (1) comprises the steps of adding a hydrosoluble salt of an alkali metal to a suspension of insoluble salts of said raw nucleic acids to solubilize the nucleic acids, removing from the resulting suspension of insolublizing cations, the addition of the hydrosoluble salt being continued until a salt concentration of not less than 1 molar in said raw nucleic acids solution is obtained.

3. A process according to claim 2, wherein the hydrosoluble salt addition is continued until said salt concentration of raw nucleic acids solution is about 3 molar.

4. A process according to claim 2, wherein hydrosoluble salt of alkali metal is selected from the group consisting of halides and acetates.

5. A process according to claim 4, wherein said salt is sodium chloride.

6. A process according to claim 5, wherein said salt is a 3 molar solution of sodium chloride.

7. A process according to claim 2, wherein the removal of the insolubilizing cation is carried out by diafiltration at a constant volume through a tangetial flow membrane with continuous make up of saline solution.

8. A process according to claim 1, wherein said membrane has a molecular weight cutoff which is not higher than 100,000.

9. A process of claim 1, wherein the step (1) pH adjustment is conducted with an acid corresponding to the anion of the solubilizing salt used to obtain the salt solution of predetermined ionic strength.

10. A process according to claim 9, wherein said acid is hydrochloric acid.

11. A process according to claim 10, wherein the hydrochloric acid is added until the solution has a hydrogen ion concentration corresponding to a pH of 3-5.

12. A process according to claim 1, wherein the depolymerization reaction of step (2) is conducted by heating at a temperature of about 70° to about 75° C.

13. A process according to claim 12, wherein the depolymerization is controlled by measuring the reversible hyperchromicity value until such value, indicated as the percent in native DNA, is 15+5.

14. A process according to claim 1, wherein the depolymerization is stopped in step 3 by cooling the solution to a temperature in the range from 15° C. to 30° C.

15. A process according to claim 1, wherein the removal of hydrogen bonds in double filament fragments of step (3) is conducted by adjusting the solution pH to a value higher than 7.

16. A process according to claim 15, wherein the solution is brought to a pH which is higher than 8.

17. A process according to claim 15, wherein the pH is adjusted by addition of an alkali metal hydroxide.

18. A process according to claim 17, wherein said alkali metal hydroxide is sodium hydroxide.

19. A process according to claim 1, wherein the solution obtained from step (3) is heated to a temperature which is 5° C. higher than the temperature of the depolymerization reaction in order to stabilize single filament fragments.

20. A process according to claim 19, wherein the heating step is conducted for at least 30 minutes.

21. A process according to claim 1, wherein the solution obtained from the stabilizing heating step (4) is hot filtered, and then any salts present in the solution are removed while still in the hot condition.

22. A process according to claim 21, wherein the solution after said salts are removed is concentrated.

23. A process according to claim 21, wherein the filtrate from the hot filtration step is subjected to dialysis through a tangential flow membrane.

24. A process according to claim 1, wherein step 1 is carried out in an acetate buffer having a molarity and a pH value corresponding to the maximum reversible hyperchromicity of the system.

25. A process according to claim 24, wherein the resulting solution from the stabilizing heating single filament fragments is filtered and the final product is precipitated by the addition of an alcoholic solvent.

26. A process according to claim 25, wherein said solvent is ethanol.

27. A process according to claim 1, wherein said salt solution of raw nucleic acids is prepared by grinding, hot proteolytic digestion, and filtration of mammalian cells to produce a lysate and concentration of the lysate, followed by addition of the salt of a cation capable of precipitating phosphates, and filtration at constant volume of the suspension, wherein said salt is selected from the group consisting of calcium chloride, calcium acetate, zinc chloride, and zinc acetate.

28. A process according to claim 27, wherein the filtration of the proteolytic lysate is carried out on a tangential flow membrane.

29. A process according to claim 28, wherein said membrane is selected to have a molecular weight cutoff of 50,000-100,000.

30. A process according to claim 27, wherein the constant volume filtration is conducted with a tangential flow membrane and with continous make-up of water.

31. A process according to claim 30, wherein said membrane has a pore size no greater than 0.45 μm.

32. A process according to claim 27, wherein the mammalian cells are selected from the group consisting of lung, intestine, liver and mucosae of sheep, swine, horses and cattle.

33. A process according to claim 27, wherein the mammalian cells are selected from the group consisting of white corpuscles or residuals of their cultures, spermatozoa, spermatocytes or germinal mammalian cells.

34. A process according to claim 27, wherein the mammalian cells are in a mother liquor arising from the processing of animal organs or tissues used in a process of obtaining heparines, proteic lysates or organ extracts.

35. A process for producing a polydeoxyribonucleotide corresponding to the following formula of random sequence:

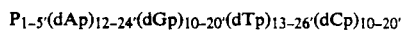

$$P_{1-5'}(dAp)_{12-24'}(dGp)_{10-20'}(dTp)_{13-26'}(dCp)_{10-20'}$$

wherein
P-phosphoric radical
dAp = deoxyadenylic monomer
dGp = deoxyguanylic monomer
dTp = deoxythymidylic monomer
dCp = deoxycytidylic monomer and having the following chemico-physical properties:
electrophoresis = homogeneous anodic mobility, extinction coefficient, $E_{1cm}^{1\%}$ at $260 \pm 1$ nm $= 220° \pm 10°$;
extinction reaction, $E_{230}E/_{260}32$ $0.45 \pm 0.04$;
coefficient of molar extinction (referred to phosphorus); $\epsilon(P) = 7.750 + 500$;
rotary power $[\alpha]_D^{20°} = 53° \pm$; and
reversible hyperchromicity, indicated as % in ** native DNA, $h = 15 + 5$;
wherein said process comprises the steps of:
(1) forming highly polymerized nicked polydeoxyribonucleotides by stabilizing an aggregation of raw nucleic acids, by adjusting, the solution of raw nucleic acids to not less than 1 molar predetermined ionic strength and adjusting the pH of said solution until the maximum reversible hyperchromicity has been reached;
(2) depolymerizing the polydeoxyribonucleotides until the reversible hyperchromicity of the solution is at a value of $h = 15 \pm 5$ measured as a percent in native DNA, by heating the resulting solution to a depolymerizing temperature for said polydeoxyribonucleotide, said depolymerizing temperature being about 60° to about 90° C., and maintaining the solution at a depolymerizing temperature until said reversible hyperchromicity value has been reached;
(3) terminating the depolymerization reaction by cooling the solution to a temperature of 15° to 30° C., and removing the hydrogen bonds in any double filament fragment in the depolymerized solution to form single filament polydeoxyribonucleotide fragments by adjusting the pH of the solution to a value between 7–8; and
(4) stabilizing the resulting filament fragments of polydeoxyribonucleotides by heating the resulting suspension to a temperature which is 5° C. higher than the temperature of the depolymerization reaction at a pH which is 0.2 higher than the pH of the depolymerization reaction, thereby preventing hydrogen bond reformation.

36. A process for producing the polydeoxyribonucleotide Defibrotide from a solution of raw nucleic acids obtained from mammalian cells, said solution being substantially free of polysaccharides and proteins, said process comprising the steps of:
(1) forming highly polymerized nicked polydeoxyribonucleotides by stabilizing an aggregation of the raw nucleic acids by adjusting the ionic strength and the pH of the solution until the maximum reversible hyperchromicity has been reached;
(2) depolymerizing the polydeoxyribonucleotides until the reversible hyperchromicity of the solution is at a value of $h = 15 \pm 5$, measured as a percent in native DNA, by heating the resulting solution to a depolymerizing temperature for the said polydeoxyribonucleotide, and maintaining the solution at a depolymerizing temperature until said specified reversible hyperchromicity value has been achieved;
(3) terminating the depolymerization reaction by cooling, and removing the hydrogen bonds in any double filament fragment in the depolymerized solution by making the medium alkaline to form single filament polydeoxyribonucleotide fragments;
(4) stabilizing the resulting single filament fragments of polydeoxyribonucleotides by heating the resulting solution at a temperature and pH higher than those of the depolymerization reaction to prevent hydrogen bond reformation, and
(5) filtering the stabilized solution of polydeoxyribonucleotides and precipitating the final product by addition of an alcohol.

37. A process for producing polydeoxyribonucleotide from a solution of raw nucleic acids obtained from mammalian cells which is substantially free of polysaccharides and proteins, wherein said polydeoxyribonucleotide corresponds to the following formula of random sequence:

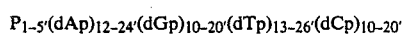

$$P_{1-5'}(dAp)_{12-24'}(dGp)_{10-20'}(dTp)_{13-26'}(dCp)_{10-20'}$$

wherein
P-phosphoric radical
dAp = deoxyadenylic monomer
dGp = deoxyguanylic monomer
dTp = deoxythymidylic monomer
dCp = deoxycytidylic monomer and having the following chemico-physical properties:
electrophoresis = homogeneous anodic mobility,
extinction coefficient, $E_{1cm}^{1\%}$ at $260 \pm 1$ nm $= 220 \pm 10°$;
extinction reaction, $E_{230}E/_{260} = 0.45 \pm 0.04$;
coefficient of molar extinction (referred to phosphorus); $\epsilon(P) = 7.750 + 500$;
rotary power $[\alpha]_D^{20°} = 53° \pm$; and
reversible hyperchromicity, indicated as % in native DNA, $h = 15 \pm 5$,
and wherein said process comprises the steps of:
(1) forming highly polymerized nicked polydeoxyribonucleotides by stabilizing an aggregation of raw nucleic acids, by adjusting the solution of raw nucleic acids to not less than 1 molar predetermined ionic strength and by adjusting the pH of said solution until the maximum reversible hyperchromicity has been reached;
(2) depolymerizing the polydeoxyribonucleotides until the reversible hyperchromicity of the solution is at a value of $h = 15 \pm 5$ measured as a percent in native DNA, by heating the resulting solution to a depolymerizing temperature for said polydeoxyribonucleotide, said depolymerizing temperature being about 60° to about 90° C., and maintaining the solution at a depolymerizing temperature until said reversible hyperchromicity value has been reached;
(3) terminating the depolymerization reaction by cooling the solution to a temperature of 15° to 30° C., and removing the hydrogen bonds in any double filament fragment in the depolymerized solution to form single filament polydeoxyribonucleotide fragments by adjusting the pH of the solution to a value between 7–8;
(4) stabilizing the resulting filament fragments of polydeoxyribonucleotides by heating the resulting suspension to a temperature which is 5° C. higher than the temperature of the depolymerization reaction at a pH which is 0.2 higher than the pH of the depolymerization reaction, thereby preventing hydrogen bond reformation, and
(5) filtering the stabilized solution of polydeoxyribonucleotides and precipitating the final product by addition of an alcoholic solvent.

* * * * *

UNITED STATES PATENT AND TRADEMARK OFFICE
CERTIFICATE OF CORRECTION

PATENT NO. : 4,985,552

DATED : January 15, 1991

INVENTOR(S) : Gianfranco FEDELI et al

It is certified that error appears in the above-identified patent and that said Letters Patent is hereby corrected as shown below:

On the cover page, Item [75], second line, "Ap iano" should read -- Appiano --; third line, "Maontovani, Villas Guardia" should read -- Mantovani, Villa Guardia --.

Column 3, line 29, "man" should read -- main --.
Column 9, line 46, "0.4" should read -- 1.04 --.
Column 13, line 3, "reaction" should read -- ratio --,
         line 3, "32" should be --=--.
         line 5, "+" should read -- ± --;
         line 6, after "±", insert -- 6 --.
Column 14, line 25, "reaction" should read -- ratio -,
         line 27, "+" should read -- ± --;
         line 28, after "±", insert -- 6 --.

Signed and Sealed this

Eleventh Day of May, 1993

*Attest:*

MICHAEL K. KIRK

*Attesting Officer*      *Acting Commissioner of Patents and Trademarks*